United States Patent [19]

Uemura et al.

[11] Patent Number: 5,138,034
[45] Date of Patent: Aug. 11, 1992

[54] METHOD OF FRACTIONATING PLASMA PROTEINS

[75] Inventors: Yahiro Uemura; Kazuo Takechi; Kenji Tanaka, all of Osaka, Japan

[73] Assignee: The Green Cross Corporation, Osaka, Japan

[21] Appl. No.: 537,651

[22] Filed: Jun. 14, 1990

[30] Foreign Application Priority Data

Jul. 12, 1989 [JP] Japan ................... 1-181672

[51] Int. Cl.$^5$ ............................ C07K 3/12; C07K 3/28
[52] U.S. Cl. .................... 530/413; 530/364; 530/380; 530/381; 530/382; 530/383; 530/384; 530/387; 530/392; 530/393; 530/394; 530/412
[58] Field of Search ............... 530/364, 380, 381, 382, 530/383, 387, 413, 830, 431, 384, 392, 393, 394, 418, 427, 412

[56] References Cited

U.S. PATENT DOCUMENTS

2,710,293 6/1955 Gerlough .......................... 530/382
4,025,618 5/1977 Garber et al. ..................... 530/383

OTHER PUBLICATIONS

Schneider et al., Vox Sang., vol. 31, pp. 141–151 (1976).
Methods of Plasma Protein Fractionation, (Academic Press, 1980), pp. 10–13, 118, 119.
Chemical Abstracts, vol. 94, 1981, p. 365, Abstract No. 99028r.
Chemical Abstracts, vol. 93, 1980, p. 425, Abstract No. 40670v.
Collen et al., Thrombosis Research, vol. 7, pp. 515–529 (1975).
Handin et al., Clin. Res. (U.S.A.), vol. 23, No. 3, p. 275A, (1975), (abstract).

*Primary Examiner*—Merrell C. Cashion, Jr.
*Assistant Examiner*—Andrew G. Rozycki
*Attorney, Agent, or Firm*—Sughrue, Mion, Zinn, Macpeak & Seas

[57] ABSTRACT

A method of fractionating plasma protein which comprises treating a plasma protein-containing material in the following sequence of steps, provided that steps (ii) through (v) may be performed in an optional order: (i) freeze-thaw treatment, (ii) treatment at 5 to 10% ethanol concentration, (iii) treatment with an anion exchanger, (iv) affinity chromatography with immobilized lysine, (v) affinity chromatography with immobilized heparin, (vi) treatment at 18 to 30% ethanol concentration, (vii) treatment at 35 to 45% ethanol concentration.

20 Claims, No Drawings

METHOD OF FRACTIONATING PLASMA PROTEINS

FIELD OF THE INVENTION

The present invention relates to a method of fractionating a plasma protein-containing material, particularly plasma, into various plasma protein fractions.

BACKGROUND OF THE INVENTION

The term "plasma protein" means any and all of more than 100 different proteins occurring in plasma. Principal plasma proteins are albumin, globulin, various blood coagulation factors, fibrinogen, fibronectin, plasminogen, prothrombin and so on. For the fractionation of plasma into these and other plasma protein fractions, such techniques as Cohn's cold ethanol fractionation, ammonium sulfate fractionation and polyethylene glycol fractionation are known.

Of these plasma proteins, albumin and globulin are particularly useful for medicinal purposes and it is, therefore, common practice to first isolate these proteins and, then, separate and recover the other proteins from the residual fraction. For example, the prior art methods described hereinbefore have been employed.

However, the yields of minor components by these techniques are invariably so low that the techniques ar inevitably inefficient in terms of the overall fractionation yield.

Under the above circumstances, the inventors of the present invention through intensive and diligent research have found that various plasma proteins can be efficiently isolated from a plasma-containing material, particularly plasma, by combining certain processes in a defined sequence. The present invention is an outcome of the above endeavor and finding.

SUMMARY OF THE INVENTION

The present invention is directed to a method for fractionating plasma protein characterized in that a plasma protein-containing material is treated by the following steps.

(i) Freeze thaw treatment
(ii) Treatment at 5 to 10% ethanol concentration
(iii) Treatment with an anion exchanger
(iv) Affinity chromatography with immobilized lysine
(v) Affinity chromatography with immobilized heparin
(vi) Treatment at 18 to 30% ethanol concentration
(vii) Treatment at 35 to 45% ethanol concentration The above steps (ii) through (v) may be carried out in an optional order.

DETAILED DESCRIPTION OF THE INVENTION

The fractionation method of the present invention can be carried out by one of the following processes comprising steps (i) through (vii).

I. (i)→(ii)→(iii)→(iv)→(v)→(vi)→(vii)
II. (i)→(ii)→(iv)→(iii)→(v)→(vi)→(vii)
III. (i)→(iii)→(ii)→(iv)→(v)→(vi)→(vii)
IV. (i)→(iii)→(iv)→(v)→(ii)→(vi)→(vii)
V. (i)→(iv)→(iii)→(v)→(ii)→(vi)→(vii)

Among these, Processes I, II and III are preferred and Process I is particularly preferred.

1. Starting material

In the present invention, a plasma protein-containing material such as blood, plasma or serum is used as the starting material. Particularly preferred is plasma.

1 2. Fractionation method

Process I (i) Freeze-thaw treatment

The plasma protein-containing material is subjected to freeze-thaw treatment to give a supernatant and a sediment. The substances which can be recovered from this sediment fraction are blood coagulation factor VIII (hereinafter referred to briefly as factor VIII) and fibronectin.

The preferred conditions of this treatment are as follows.
Freezing conditions:
 $-10°$ to $-40°$ C., particularly $-20°$ to $-30°$ C.; at least 1 hour, for example up to one month.
Thawing conditions: 0° to 5° C.
Separating conditions:
 Filtration or centrifugation (1,000 to 3,000 rpm, 10 minutes), 0° to 5° C.

(ii) Treatment at 5 to 10% ethanol concentration

The supernatant separated under (i) is treated to obtain a 5 to 10% ethanol concentration, preferably 7 to 9% ethanol, and the supernatant fraction is separated from the sediment fraction. The substances which can be recovered from the sediment fraction are fibrinogen and blood coagulation factor XIII (hereinafter referred to as factor XIII).

The preferred conditions of this treatment are as follows.
Conditions of ethanol treatment:
 5° to 3° C. (particularly $-2°$ to $-3°$ C.), pH 6.8 to 7.4; 30 minutes to 15 hours, particularly 1 to 5 hours)
Separating conditions:
 centrifugation (1,000 to 8,000 rpm, 10 to 30 minutes), 0° to 5° C.

(iii) Treatment with an anion exchanger

The supernatant obtained from step (ii) is treated with an anion exchanger to separate an unadsorbed fraction from an adsorbed fraction. The substances which can be eluted from the adsorbed fraction are prothrombin, blood coagulation factor IX (hereinafter referred to as factor IX) and protein C. The anion exchanger includes, among others, DEAE series available from Pharmacia (e.g. DEAE-agarose, DEAE-dextran, DEAE-cellulose, etc.), QAE series available from Pharmacia (e.g. QAE-agarose, QAE-dextran, etc.) and so on. This treatment can be carried out either by way of column chromatography or a batchwise separation, with being the latter preffered.

The preferred conditions of this treatment are as follows.
Contacting conditions: pH 6 to 8, 2° to 20° C.
Eluting conditions:
 pH 4 to 8, 2° to 20° C., ionic strength 0.005 to 0.5M (particularly 0.01 to 0.2M). Examples of eluting solutions are phosphate buffer and physiological saline.

(iv) Treatment with immobilized lysine

The unadsorbed fraction from step (iii) is subjected to affinity chromatography with immobilized lysine to give an adsorbed fraction and an unadsorbed fraction. The substance which can be eluted from the adsorbed fraction is plasminogen. The immobilized lysine may for example be lysine-agarose. The process for preparation thereof is disclosed in Science, 170, 1095 (1970), for instance. This treatment can be carried out either by way of column chromatography or a batchwise separation, with being the latter preffered.

The preferred conditions of this treatment are as follows.
Contacting conditions: pH 6 to 8, 2° to 20° C.
Eluting conditions:
  a solution of EACA (e-amino-caproic acid, 0.1 to 0.4M) or lysine (0.1 to 0.4M), pH 6 to 8, 2° to 20° C.

(v) Treatment with immobilized heparin

The unadsorbed fraction from step (iv) is subjected to affinity chromatography with immobilized heparin to give an unadsorbed fraction and a adsorbed fraction. Anti-thrombin-III can be eluted from the adsorbed fraction. The immobilized heparin may for example be heparin-agarose available from Pharmacia. This treatment can be carried out either by way of column chromatography or a batchwise separation, with being the latter preffered.
Contacting conditions:
  pH 6 to 8 (particularly pH 7 to 7.5), 2 to 20° C.
Eluting conditions:
  pH 6 to 8 (particularly pH 7 to 7.5), inonic strength 1 to 3M (particularly 1.5 to 2M), 2° to 20° C.

(vi) Treatment at 18 to 30% ethanol concentration

The unadsorbed fraction from step (v) is treated to obtain a 18 to 30% ethanol concentration, preferably 20 to 25% ethanol, and the resulting supernatant fraction is separated from the sediment fraction. Immunoglobulins can be recovered from the sediment fraction.
Conditions of ethanol treatment:
  pH 4.5 to 8 (particularly pH 5.2 to 7), 0 to −7° C. (particularly −5° to −6° C.), 0.5 to 15 hours (particularly 1 to 5 hours)
Separating conditions:
  The same as those for recovery of fraction II+III in Cohn's cold ethanol fractionation.
  For example, centrifugal separation (5,000 to 20.000 rpm, 10 to 30 minutes, 0° to 5° C.) is preferred.

(vii) Treatment at 35 to 45% ethanol concentration

The supernatant from step (vi) is treated to obtain a 35 to 45% ethanol concentration and the supernatant is separated from the sediment. Haptoglobin and transferrin can be recovered from the sediment fraction, and albumin from the supernatant fraction.
Conditions of ethanol treatment:
  pH 5 to 7 (particularly pH 5.8 to 6.3), 0° to −7° C. (particularly −6° to −5° C.), 0.5 to 15 hours (particularly 1 to 5 hours)
Separating conditions:
  The same as those for recovery of fractions $IV_1$+$IV_4$+albumin in Cohn's ethanol fractionation. For example, centrifugal separation (5,000 to 20,000 rpm, 10 to 30 minutes, 0° to 5° C.) is preferred.

Process II

The steps (i), (ii), (vi) and (vii) are conducted in the same manner as in Process I.

(iv) Treatment with immobilized lysine

The supernatant from step (ii) is subjected to affinity chromatography with immobilized lysine to give an adsorbed fraction and an unadsorbed fraction.

(iii) Treatment with an anion exchanger

The unadsorbed fraction from step (iv) is treated with an aninon exchanger to separate an unadsorbed fraction from an adsorbed fraction.

(v) Treatment with immobilized haparin

The unadsorbed fraction from step (iii) is subjected to affinity chromatography with immobilized heparin to give an unadsorbed fraction and an adsorbed fraction.

Process III

The steps (i), (v), (vi) and (vii) are conducted in the same manner as in Process I.

(iii) Treatment with an anion exchanger

The supernatant from step (i) is treated with an anion exchanger to separate an unadsorbed fraction from an adsorbed fraction.

(ii) Treatment at 5 to 10% ethanol concentration

The unadsorbed fraction from step (iii) is treated at 5 to 10% ethanol concentration and the supernatant fraction is separated from the sediment fraction.

(iv) Treatment with immobilized lysine

The supernatant from step (ii) is subjected to affinity chromatography with immobilized lysine to give an adsorbed fraction and an unadsorbed fraction.

Process IV

The steps other than described below can be carried out in the same manner as in Process I.

(iii) Treatment with an anion exchanger

The supernatant from step (i) is treated with an anion exchanger to separate an unadsorbed fraction from an adsorbed fraction,.

(ii) Treatment at 5 to 10% ethanol concentration

The unadsorbed fraction from step (v) is treated at 5 to 10% ethanol concentration and the supernatant fraction is separated from the sediment fraction.

(vi) Treatment at 18 to 30% ethanol concentration

The supernatant fraction from step (ii) is treated at 18 to 30% ethanol concentration and the resulting supernatant fraction is separated from the sediment fraction.

Process V

The steps other than described below can be carried out in the same manner as in Process I.

(iv) Treatment with immobilized lysine

The supernatant from step (i) is subjected to affinity chromatography with immobilized lysine to give an adsorbed fraction and unadsorbed fraction.

(iii) Treatment with an anion exchanger

The unadsorbed fraction from step (iv) is treated with an anion exchanger to separate an unadsorbed fraction from an adsorbed fraction.

(v) Treatment with immobilized heparin

The unadsorbed fraction from step (iii) is subjected to affinity chromatography with immobilized heparin to give an unadsorbed fraction and an adsorbed fraction.

(ii) Treatment at 5 to 10% ethanol concentration

The unadsorbed fraction from step (v) is treated at 5 to 10% ethanol concentration and the supernatant fraction is separated from the sediment fraction.

(vi) Treatment at 18 to 30% ethanol concentration

The supernatant fraction from step (ii) is treated at 18 to 30% ethanol concentration and the resulting supernatant fraction is separated from the sediment fraction.

3. Purification methods

The plasma protein fractions thus obtained are respectively purified by the per se known techniques.

(i) Factor VIII and fibronectin

A method for isolation and purification of factor VIII is described in EP-A-117064 and U.S. Pat. No. 4,822,872 or EP-A-245872. The polyethylene glycol fractionation method (U.S. Pat. No. 3,631,018), glycine sedimentation method (U.S. Pat. No. 3,652,530), anion exchanger method (U.S. Pat. No. 4,093,608), etc. can also be employed. Methods for isolation and purification of fibronectin are described, for example, in U.S. Pat. No. 4,424,206 or EP-A-58993, U.S. Pat. No. 4,565,651 or EP-A-106608 and JP-A-58-121220 (the term "JP-A" as used herein means "an unexamined published Japanese patent application").

(ii) Fibrinogen and factor XIII

Methods for isolation and purification of fibrinogen are described, for example, in JP-A-62-89628 and 64-19023 or DE-A 3813464. Methods for isolation and purification of factor XIII are described, for example, in JP-A 56 166121 and 53 72811.

(iii) Factor IX, prothrombin and protein C

Methods for isolation and purification of factor IX are disclosed, for example, in JP-A-62-10019 and 63-48720.

Regarding the purification of prothrombin, the method utilizing its adsorptive affinity for an inorganic salt, the method using an anion exchanger, and the affinity chromatographic method are known, for example from the following publications.

J. Biol. Chem., 174, 565 (1954)
Am. J. Physiol., 172, 731 (1953)
Japan J. Biochem., 40(12), 890–901 (1968)
JP-B-58-50202 (the term "JP-B" as used herein means "an examined published Japanese patent application".)
J. Biol. Chem., 234, 2857 (1959)
JP-A-63 290829 (DE-A-3809991)

For the purification of protein C, there are known the barium chloride precipitation-adsorption method, ammonium sulfate fractionation method, anion exchanger treatment, preparative electrophoresis, anti protein C antibody column chromatography, anti-impurity protein antibody column chromatography and so on [J. Biol. Chem., 251, 355–363 (1976), ibido, 258, 1914–1920 (1983), J. Nara Med. Ass., 35, 448–454 (1984), J. Biol. Chem., 261, 11097–11105 (1986), Thromb. Haemostas., 48, 1–5 (1983), JP-A-1-226900].

(iv) Antithrombin-III

Methods for isolation and purification of antithrombin-III are disclosed in U.S. Pat. No. 3,842,061 or DE-A-2243688 and U.S. Pat. No. 4,340,589 or GB-A-2064545.

(v) Plasminogen

Methods for isolation and purification of plasminogen are disclosed in Science, 170, 1095 (1970) and JP-A-55-153592, 63-239300, U.S. Pat. Nos. 4,361,652 and 4,361,653.

(vi) Immunoglobulins

For example, the methods described in JP-A-53-47515, and 63-183539 or EP-A-246579, U.S. Pat. Nos. 4,371,520 and 4,093,606, etc., may be employed. Heat treatment is also a preferred procedure. Thus, for wet heating, the methods described in JP-A-61-191622 or EP-A-196761 and U.S. Pat. No. 4,845,199 or EP-A 253313, and for dry heating, the methods described in JP-A-62-283933, 62-289523, 62-228024 or EP-A-225581 and U.S. Pat. No. 4,721,777 or EP-A-177836 can be employed.

(vii) Haptoglobin

The methods disclosed in U.S. Pat. Nos. 4,061,735 and 4,137,307, and JP-A-63-17889 can be employed.

(viii) Albumin

As methods for purification of albumin, ethanol fractionation (JP-B-35 5297 and 47-2869) and heat treatment (JP-B-43-1604 and 51-40132) may be mentioned as examples.

Thus, in accordance with the method of the present invention, the plasma protein in a plasma protein-containing material, such as plasma in particular, can be efficiently fractionated into various component plasma proteins.

Table 1 shows the efficiencies of recovery of various plasma proteins by the method of the invention.

TABLE 1

| Plasma protein fraction | Relative ratio of recovery rate |
| --- | --- |
| Fractor VIII | x 1 |
| Fibronectin | * |
| Fibrinogen | x 1 |
| Factor XIII | * |
| Plasminogen | x 3 |
| Thrombin | x 3 |
| Factor IX | x 1 |
| Protein C | * |
| Antithrombin-III | x 3 |
| Immunoglobulin G | x 1 |
| Immunoglobulin A | x 1 |
| Immunoglobulin M | x 1 |
| Haptoglobin | x 1 |
| Transferrin | x 1 |
| Albumin | x 1 |

The method of the invention and the conventional method for recovery of various plasma proteins are schematically shown in Tables 2 and 3, respectively.

TABLE 2(1)
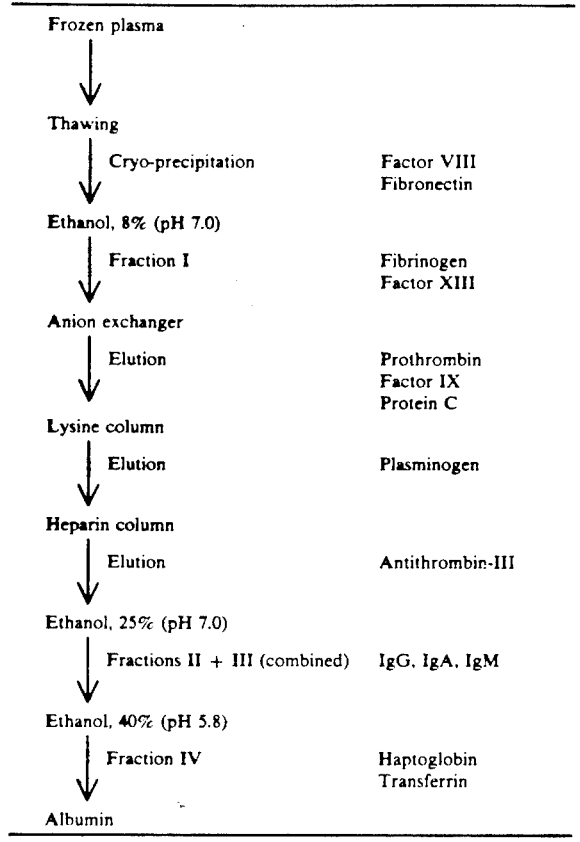
TABLE 2(2)
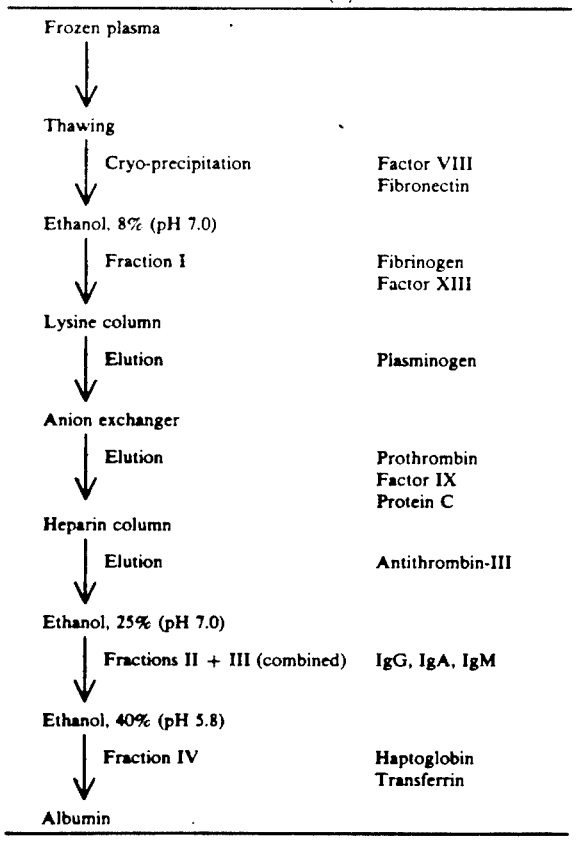
TABLE 2(3)
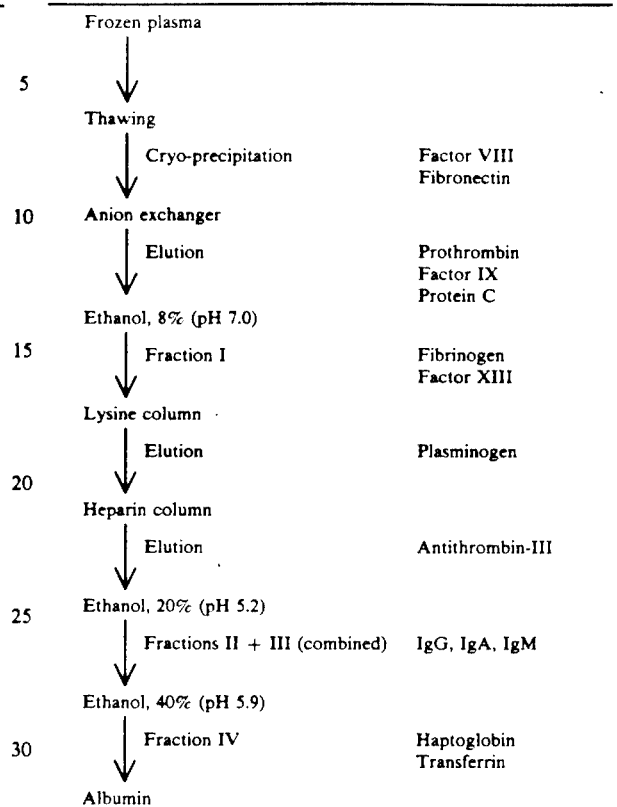
TABLE 3
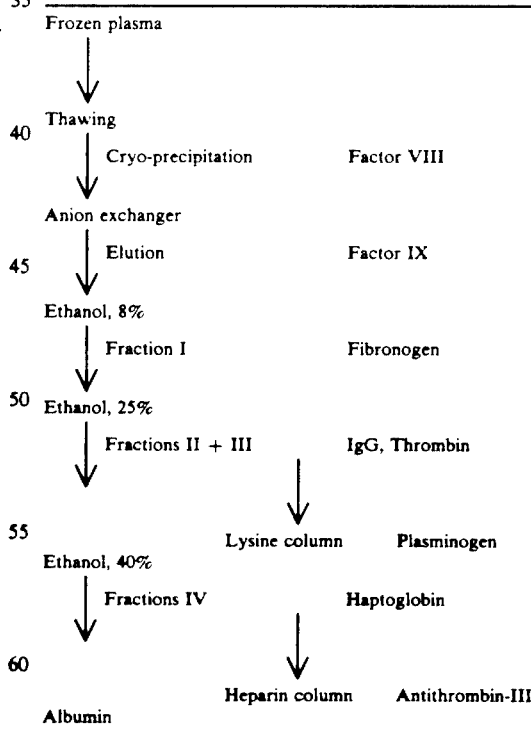
EXAMPLE
HBsAg-negative, HIV antibody-negative normal human blood was collected using sodium citrate as an anticoagulant and centrifuged to separate the plasma.

This plasma was immediately chilled to a temperature not more than −30° C. A 10 l portion of thus-frozen plasma was gradually thawed in a cold chamber at 2° to 10° C. and when the plasma temperature has risen to 1° to 3° C., the plasma was immediately centrifuged to recover the insolubles (cryo-precipitate).

The supernatant was diluted with 53% ethanol previously chilled to −20° C. to a final ethanol concentration of 8%. The temperature of the dilution was −1° to 1° C. and the pH of the dilution was 7.0. The dilution was allowed to stand under the same conditions for 2 hours and, then, centrifuged at 3,000 rpm for 20 minutes to recover the sediment (fraction I).

A column with a diameter of 10cm was packed with 1 kg (wet weight) of Sepharose Q Fast Flow available from Pharmacia equilibrated with 0.02M sodium chloride and the centrifugal supernatant was passed through the column at a temperature of 4° to 10° C. and a flow rate of 2 l/hr, whereby prothrombin, factor IX, protein C, etc., were adsorbed. The clear effluent emerging from the Sepharose Q Fast Flow column was passed successively through a lysine Sepharose column (10 cm in diameter, 2 (cf. Science, 170, 1095 (1970)) and a heparin-Sepharose column (10 cm in diameter, 0.5 l) (cf. Biochem. J., 124, 677 (1971)). As a result, plasminogen was adsorbed on the lysine-Sepharose column, and antithrombin-III on the heparin-Sepharose column.

The effluent was diluted with ethanol chilled to −20° C. to a final ethanol concentration of 25%. The dilution was allowed to stand at pH 7.0 and −3° C. for 2 hours and the resulting precipitate (fractions II+III) was separated by centrifuging at 10,000 rpm for 20 minutes. The supernatant was recovered.

The supernatant was further diluted with ethanol chilled to −30° C. to a final ethanol concentration of 40%, and the dilution at pH 5.8 was allowed to stand at −5° C. for 2 hours, and, then, centrifuged at 10,000 rpm for 20 minutes. The precipitate (fraction IV) and the supernatant were independently recovered.

REFERENCE EXAMPLE

(1) Purfication of factor VIII and fibronectin from cryoprecipitate

The cryo-precipitate was suspended in distilled water for injection containing 100 IU/ml of heparin and extracted at 20°~30° C. To the extract was added aluminum hydroxide gel to remove prothrombin by adsorption, followed by addition of 0.3% TNBP (chemical name: tri-n-butyl phosphate)/1% Tween 80 for 6-hour virus inactivation at 30° C. Thereafter, fibrinogen was precipitated by 2M glycine fractionation and the supernatant was recovered. To this supernatant was added 1.5M sodium chloride to recover factor VIII in the precipitate fraction and fibronectin in the supernatant fraction. The factor VIII was further purified by gel chromatography. The fibronectin was recovered by cooling the supernatant and precipitating it with 3M sodium chloride.

(2) Purfication of factor XIII-containing fibrinogen from Fraction I

The precipitate of Fraction I was dissolved in 0.9% sodium chloride solution followed by the addition of 5% EACA (ε-amino-caproic acid) as a protease inhibitor and 0.3% TNBP/1% Tween 80 as a virus inactivator for 6-hour inactivation at 30° C. Then, 2M glycine was added to recover factor XIII-containing fibrinogen as a precipitate.

(3) Elution of prothrombin, factor IX and protein C from Sepharose Q Fast Flow The above-mentioned Sepharose Q Fast Flow was suspended in 20 mM Tris-buffer (pH 7.15) and packed into a column with a diameter of 10 cm. After the column was washed with 2 volumes (based on column capacity; the same applies hereinafter) of the same solvent, factor IX was eluted with 2 volumes of 0.3M sodium chloride solution at pH 7.15.

Then, prothrombin was eluted by passing 2 volumes of 0.35M sodium chloride solution at pH 7.15. Thereafter, protein C was eluted with 2 volumes of 0.4M sodium chloride solution at pH 7.15.

(3-1) To the prothrombin fraction were added thromboplastin and fresh human plasma for conversion to thrombin. To this crude thrombin solution were added 4% EACA as a protease inhibitor and 0.3% TNBP/1% Tween 80 as a virus inactivator and the inactivation treatment was carried out at 30° C. for 6 hours. Then, the thrombin was adsorbed on SP-Sephadex (Pharmacia) for purification.

(3-2) The factor IX fraction was applied to an anti-IX mouse monoclonal antibody-conjugated gel for adsorption of factor IX. Prothrombin was recovered in the unadsorbed fraction. The factor IX adsorbed on the antibody-conjugated gel was eluted with glycine-HCl buffer at pH 2.5 and neutralised with sodium hydroxide, followed by removal of a trace amount of IgG mouse with anti-mouse IgG antibody.

(3-3) Purification of protein C i) Dialysis was carried out with 20 mM sodium acetate buffer at pH 5.0. The dialysate was centrifuged at 10,000 G for 20 minutes and the supernatant fraction was recovered.

ii) Cation exchange chromatography

The supernatant fraction was added to Bakerbond CBX (J. T. Baker). As a starting buffer, 20 mM sodium acetate buffer at pH 5.0 was used and as an eluent buffer, 1M sodium chloride−20 mM sodium acetate at pH 5.0 was used. After addition of the sample, the system was washed with the starting buffer and, then, the elution buffer was run. The effluent was recovered.

iii) Anion exchange chromatography

The dialysate was added to Mono Q HR 60/10 (or Q Sepharose High Performance 60/100) (Pharmacia). As a starting buffer, 20 mM Tris-HCl buffer at pH 7.15 was used and as an eluent buffer, 1M sodium chloride−20 mM Tris-HCl buffer, at pH 7.15 was used. After addition of the sample, the system was washed with 30% (v/v) eluent buffer-starting buffer, followed by elution on a linear gradient of 30% 40% eluent buffer/starting buffer to recover the active fraction.

iv) Gel chromatography

The dialysate was added to Superose 12 prep grade 60/600 (Pharmacia). As an eluent buffer, 20 mM Tris-HCl-500 mM sodium chloride buffer (pH 7.2) was used and the active fraction was recovered.

v) Dextran sulfate chromatography

The dialysate was added to Sepharose CL4B (Pharmacia) with dextran sulfate as a ligand. As a starting buffer, 25 mM imidazole at pH 6 was used and as an eluent buffer, 1M sodium chloride−25 mM imidazole at pH 6.0 was used. After addition of the sample, elution was carried out on a linear gradient of 0%→50% eluent buffer/starting buffer and the active fraction was recovered.

vi) Reversed phase chromatography

The fraction obtained was applied to a reversed phase column with C8 (Chemco) as a ligand. Stock solutions A (distilled water containing 0.1% tetrafluoroacetic acid) and B (800 ml of acetonitrile diluted with stock solution A to make 1,000 ml) were prepared and 400 ml of stock solution B was diluted with stock solution A to make 1,000 ml (the final concentration of acetonitrile: 32%) for use as a starting buffer. On the other hand, 500 ml of stock solution B was diluted with stock solution A to make 1,000 ml (the final concentration of acetonitrile: 40%) for use as an eluent buffer. After the column was washed with the starting buffer, elution was carried out on a linear gradient of 0%→50% eluent buffer (actual acetonitrile concentration 32%→36%). From the fractions thus obtained, the organic solvent was evaporated under reduced pressure.

(4) Purification of plasminogen from lysine-Sepharose

The lysine-Sepharose column on which plaminogen had been adsorbed was washed with 2 volumes of 0.9% sodium chloride solution and the same amount of 1.0M sodium chloride solution in that order to remove impurity protein. Elution of plasminogen was carried out with 0.2M EACA solution (pH 7.0). This plasminogen fraction was concentrated to 200 UI/ml by means of an ultrafiltration membrane with a cutoff molecular weight of 30,000. To this concentrate was added aprotinin (final concentration 50 U/ml) and the mixture was heated at 60° C. for 10 hours.

The mixture was dialysed overnight against a solvent containing 0.05M phosphate buffer, 0.05M sodium chloride and 0.2% lysine to give a lysyl-type plasminogen. The dialysate was filtered through a bacterial filter and lyophilized.

This product was re-dissolved to a concentration of 250 IU/ml and a pyrogen test was carried out by dosing rabbits intravenously with 1 ml/kg of the solution. As a result, the product met the test of the Minimum Requirements for Biological Products.

(5) Purification of antithrombin-III from heparin-Sepharose

The heparin-Sepharose column on which antithrombin-III had been adsorbed was washed with 4 volumes of 0.4M sodium chloride solution (pH 7.0) and then, antithrombin-III was eluted with 2M sodium chloride solution (pH 7.0).

To this aqueous solution of antithrombin-III was added sodium citrate to a concentration of 0.6M, and after the pH was adjusted to 7.8, the solution was heat-treated at 60° C. for 10 hours. Then, sodium chloride (final concentration 3M) and sodium citrate (final concentration 20 mM) were added to bring the pH to 7.5. On the other hand, the aqueous solution containing antithrombin-III was contacted with a butyl type polyvinyl carrier (Butyl-Toyopearl 650, Tosoh Corporation) equilibrated with 20 mM sodium citrate buffer containing 3M sodium chloride (pH 7.5) and developed with the above buffer and the unadsorbed fraction was recovered. Then, it was dialysed against 0.9% sodium chloride solution overnight to give a 1 (w/v)% aqueous solution of antithrombin-III. This solution was filtered or centrifuged as necessary, to give a clear solution.

(6) Purification of IgG from Fraction II+III

In 30 l of cold distilled water was suspended 10 kg of Fraction II+III (pH 5.5), and after through stirring, the suspension was centrifuged to recover a clear supernatant. To this supernatant was added 500 g/l of sorbitol and the mixture was heat-treated at 60° C. for 10 hours at pH 5.5. The heated mixture was diluted with cold distilled water to 3 to 5 volumes and polyethylene glycol 4000 was added to a final concentration of 5%. The resulting precipitate was removed by centrifugation.

The supernatant was adjusted to pH 8.0 and polyethylene glycol 4000 was added to a concentration of 12%. The precipitated IgG was recovered.

(7) Purification of haptoglobin from Fraction IV

In 140 l of 0.05M ammonium acetate buffer at pH 8.2 was suspended 30 kg of Fraction IV, followed by addition of ammonium sulfate to 35% saturation. The precipitate formed was removed by centrifugation. After the supernatant was adjusted to pH 7.5, 1 kg of light silicic anhydride (Aerosil: Degussa Corporation) was added and the mixture was stirred at room temperature for 1 hour. The mixture was then centrifuged and the supernatant was recovered. In the supernatant, 70% of haptoglobin was recovered and the turbidity of the solution could be completely removed.

(8) Purification of albumin

The purification was carried out according to Cohn's cold ethanol fractionation process 6.

i) The supernatant was treated with 40% ethanol at pH 4.8 and −5° C. and the resulting sediment was recovered (Fraction V).

ii) The sediment was dissolved in a suitable solvent and treated with 10% ethanol at pH 4.5 and −3° C. and the supernatant was recovered.

iii) The supernatant was treated with 40% ethanol at pH 5.2 and −5° C. and the resulting sediment was recovered to give pure albumin.

While the invention has been described in detail and with reference to specific embodiments thereof, it will be apparent to one skilled in the art that various changes and modifications can be made therein without departing from the spirit and scope thereof.

What is claimed is:

1. A method of fractionating blood, plasma or serum which comprises treating a plasma protein-containing blood, plasma or serum with the following sequence of steps:
 (i) freezing and then thawing the material and recovering a supernatant and a sediment, wherein factor VIII and fibronectin are obtained from the sediment,
 (ii) treating the supernatant at a 5–10% ethanol concentration and recovering a supernatant a sediment, wherein fibrinogen and factor XIII are obtained from the sediment,
 (iii) treating the supernatant from step (ii) with an anion exchanger and recovering an adsorbed and an unadsorbed fraction, wherein prothrombin, factor IX and protein C are obtained from the adsorbed fraction,
 (iv) carrying out affinity chromatography with immobilized lysine on the unadsorbed fraction from step (iii) and recovering an adsorbed and an unadsorbed fraction therefrom, wherein plasminogen is obtained from the adsorbed fraction, (v) carrying out affinity chromatography with immobilized heparin on the unadsorbed fraction obtained from step (iv), and recovering an adsorbed and an unadsorbed fraction therefrom, wherein antithrombin-III is obtained from the adsorbed fraction, (vi) treating the unadsorbed fraction from step (v) at 18 to 30% ethanol concentration and recovering a supernatant and a sediment, wherein IgG, IgA and IgM are obtained from the sediment, and (vii) treating the supernatant from step (vi) at 35 to 45% ethanol concentration and thereafter recovering a supernatant and a sediment, wherein haptoglobin and transferrin are obtained from the sediment, and albumin is obtained from the supernatant.

2. A method of fractionating blood, plasma or serum which comprises treating a plasma protein-containing blood, plasma or serum with the following sequence of steps:

(i) freezing and then thawing the material and recovering a supernatant and a sediment, wherein factor VIII and fibronectin are obtained from the sediment, (ii) treating the supernatant at a 5–10% ethanol concentration and recovering a supernatant and a sediment, wherein fibrinogen and factor XIII are obtained from the sediment, (iii) carrying out affinity chromatography with immobilized lysine on the supernatant obtained from step (ii) and recovering an adsorbed and an unadsorbed fraction, wherein plasminogen is obtained from the adsorbed fraction, (iv) treating the unadsorbed fraction obtained from step (iii) with an anion exchanger and recovering an adsorbed and an unadsorbed fraction therefrom, wherein prothrombin, factor IX and protein C are obtained from the adsorbed fraction, (v) carrying out affinity chromatography with immobilized heparin on the unadsorbed fraction obtained from step (iv), and recovering an adsorbed and an unadsorbed fraction therefrom, wherein antithrombin-III is obtained from the adsorbed fraction, (vi) treating the unadsorbed fraction from step (v) at 18 to 30% ethanol concentration and recovering a supernatant and a sediment, wherein IgG, IgA and IgM are obtained from the sediment, and (vii) treating the supernatant from step (vi) at 35 to 45% ethanol concentration and thereafter recovering a supernatant and a sediment, wherein haptoglobin and transferrin are obtained from the sediment, and albumin is obtained from the supernatant.

3. The process of claim 1, wherein the plasma protein-containing material is plasma.

4. The process of claim 2, wherein the plasma protein-containing material is plasma.

5. The process of claim 1, wherein step (i) is carried out at a freezing condition of −10° to −40° C. for 1 hour to 1 month, and the thawing is carried out at 0° to 5° C.

6. The process of claim 2, wherein step (i) is carried out at a freezing condition of −10° to −40° C. for 1 hour to 1 month, and the thawing is carried out at 0° to 5° C.

7. The process of claim 1, wherein the treatment at 5–10% ethanol concentration is carried out at 5° to −3° C. and at a pH of 6.8–7.4 for 30 minutes to 15 hours.

8. The process of claim 2, wherein the treatment at 5–10% ethanol concentration is carried out at 5° to −3° C. and at a pH of 6.8–7.4 for 30 minutes to 15 hours.

9. The process of claim 1, wherein the treatment with the anion exchanger is carried out at a pH of 6 to 8.

10. The process of claim 2, wherein the treatment with the anion exchanger is carried out at a pH of 6 to 8.

11. The process of claim 1, wherein the affinity chromatography with immobilized lysine is carried out at a pH of 6 to 8.

12. The process of claim 2, wherein the affinity chromatography with immobilized lysine is carried out at a pH of 6 to 8.

13. The process of claim 1, wherein the affinity chromatography with immobilized heparin is carried out at a pH of 6 to 8.

14. The process of claim 2, wherein the affinity chromatography with immobilized heparin is carried out at a pH of 6 to 8.

15. The process of claim 1, wherein the treatment at 18 to 30% ethanol concentration is carried out at a pH of 4.5 to 8, at a temperature of 0° to −7° C., for about 0.5 to 15 hours.

16. The process of claim 2, wherein the treatment at 18 to 30% ethanol concentration is carried out at a pH of 4.5 to 8, at a temperature of 0° to −7° C., for about 0.5 to 15 hours.

17. The process of claim 1, wherein the treatment at 35 to 45% ethanol concentration is carried out at a pH of 5 to 7, at a temperature of 0° to −7° C., for about 0.5 to hours.

18. The process of claim 2, wherein the treatment at 35 to 45% ethanol concentration is carried out at a pH of 5 to 7, at a temperature of 0° to −7° C., for about 0.5 to 15 hours.

19. A method of fractionating blood, plasma or serum which comprises treating a plasma protein-containing blood, plasma or serum with the following sequence of steps:

(i) freezing and then thawing the material and recovering a supernatant and a sediment, wherein factor VIII and fibronectin are obtained from the sediment, (ii) treating the supernatant with an anion exchanger and recovering an adsorbed and an unadsorbed fraction, wherein prothrombin, factor IX and protein C are obtained from the adsorbed fraction, (iii) treating the unadsorbed fraction from step (ii) at a 5 to 10% ethanol concentration and recovering a supernatant and a sediment, wherein fibrinogen and factor XIII are obtained from the sediment, (iv) carrying out affinity chromatography with immobilized lysine on the unadsorbed fraction from step (iii) and recovering an adsorbed and an unadsorbed fraction therefrom, wherein plasminogen is obtained from the adsorbed fraction, (v) carrying out affinity chromatography with immobilized heparin on the unadsorbed fraction obtained from step (iv), and recovering an adsorbed and an unadsorbed fraction therefrom, wherein antithrombin-III is obtained from the adsorbed fraction, (vi) treating the unadsorbed fraction from step (v) at 18 to 30% ethanol concentration and recovering a supernatant and a sediment, wherein IgG, IgA and IgM are obtained from the sediment, and (vii) treating the supernatant from step (vi) at 35 to 45% ethanol concentration and thereafter recovering a supernatant and a sediment, wherein haptoglobin and transferrin are obtained from the sediment, and albumin is obtained from the supernatant.

20. The process of claim 1, wherein said plasma protein-containing blood, plasma or serum comprises factor VIII, fibronectin, prothrombin, factor IX, protein C, fibrinogen, factor XIII, palsminogen, antithrombin-III, globulin, haptoglobin, transferrin and albumin.

* * * * *